United States Patent [19]

Croisier et al.

[11] 4,080,449
[45] Mar. 21, 1978

[54] 1,2,4,5-TETRAHYDRO-3H-2-BENZAZEPIN-3-ONES

[75] Inventors: Paul Croisier, Waterloo; Ludovic Rodriquez, Brussels, both of Belgium

[73] Assignee: U C B, Societe Anonyme, Brussels, Belgium

[21] Appl. No.: 819,279

[22] Filed: Jul. 27, 1977

[30] Foreign Application Priority Data

Jul. 30, 1976   United Kingdom .............. 31846/76

[51] Int. Cl.² ................... C07D 223/16; A61K 31/55
[52] U.S. Cl. .............................. 424/244; 260/239.3 B
[58] Field of Search .................. 260/239.3 B; 424/244

[56] References Cited

PUBLICATIONS

Wittekind et al., "J. Het. Chem.," vol. 8, pp. 495–501 (1971).

*Primary Examiner*—Henry R. Jiles
*Assistant Examiner*—Robert T. Bond
*Attorney, Agent, or Firm*—Wenderoth, Lind & Ponack

[57] ABSTRACT

New physiologically active 1,2,4,5-tetrahydro-3H-2-benzazepin-3-ones having the general formula

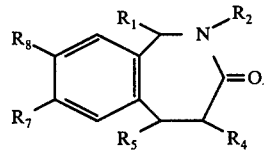

wherein $R_1$ is hydrogen or phenyl, $R_2$ is hydrogen, alkyl, $C_3$-$C_6$-alkenyl, $C_1$-$C_4$-acyl, hydroxyalkyl, alkoxyalkyl, mono- or dialkylaminoalkyl, cyanoalkyl, alkoxyacetyl, carbamoylalkyl, acetamido-$C_2$-$C_5$-alkyl, alkoxycarbonylalkyl or (tetrahydro-2H-pyran-2-yloxy)alkyl, the alkyl and the alkoxy radicals having 1 to 5 carbon atoms, $R_4$ is hydrogen or $C_1$-$C_4$-alkyl, $R_5$ is hydrogen, $C_1$-$C_4$-alkyl or phenyl, $R_7$ is hydrogen, halogen or $C_1$-$C_4$-alkoxy and $R_8$ is hydrogen, halogen or $C_1$-$C_4$-alkyl, at least one of the symbols $R_1$ to $R_8$ being other hydrogen, processes for the preparation thereof and pharmaceutical compositions containing the same. In particular, the compounds of this invention are useful in the treatment of memory disorders.

13 Claims, No Drawings

1,2,4,5-TETRAHYDRO-3H-2-BENZAZEPIN-3-ONES

The present invention relates to new physiologically active 1,2,4,5-tetrahydro-3H-2-benzazepin-3-ones, to processes for the preparation thereof and to pharmaceutical compositions containing the same.

The new 1,2,4,5-tetrahydro-3H-2-benzazepin-3-ones according to the present invention are compounds of the general formula:

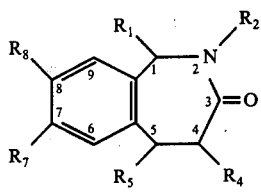

wherein
- $R_1$ is a hydrogen atom or a phenyl radical,
- $R_2$ is a hydrogen atom, a straight-chain or branched-chain alkyl radical, an alkenyl radical having 3 to 6 carbon atoms, an acyl radical having 1 to 4 carbon atoms, a hydroxyalkyl, alkoxyalkyl, monoalkylaminoalkyl, dialkylaminoalkyl, cyanoalkyl, alkoxyacetyl, carbamoylalkyl, acetamidoalkyl, alkoxycarbonylalkyl or (tetrahydro-2H-pyran-2-yloxy)alkyl radical, the alkyl and the alkoxy radicals having 1 to 5 carbon atoms, except in the case of the acetamidoalkyl radical where the alkyl radical has 2 to 5 carbon atoms,
- $R_4$ is a hydrogen atom, an alkyl radical having 1 to 4 carbon atoms,
- $R_5$ is a hydrogen atom, an alkyl radical having 1 to 4 carbon atoms or a phenyl radical,
- $R_7$ is a hydrogen or halogen atom or an alkoxy radical having 1 to 4 carbon atoms,
- $R_8$ is a hydrogen or halogen atom or an alkyl radical having 1 to 4 carbon atoms, at least one of the symbols $R_1$ to $R_8$ being other than a hydrogen atom.

The 1,2,4,5-tetrahydro-3H-2-benzazepin-3-one system (I), even when unsubstituted, is a recent acquisition in chemistry, because, although it was first mentioned in 1949 as the product resulting from a Schmidt rearrangement of 3,4-dihydro-2(1H)-naphthalenone (see I. L. Knunyants and B. P. Fabrichnyi, Doklady Akad.Nauk S.S.S.R.68,(1949),523-6):

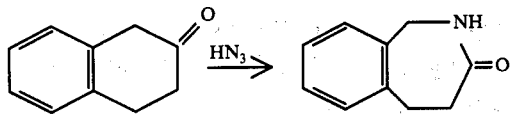

and having a melting point of 109°-110° C. (after recrystallization from water), it has recently been proved that this product was actually a mixture (see A. N. Kost and A. P. Stankevicius, Chem. Het. Compounds, 7/9 (1971), 1288-92). French Patent Specification No. 1,472,930, dealing with the same reaction, also gives, as melting point, that of the mixture. It was not until the publication of the work of A. P. Stankevicius and A. N. Kost (Russian Patent Specification No. 190,365 and the article by A. N. Kost and A. P. Stankevicius, loc.cit.) that a process was known which leads unambiguously to the desired lactam:

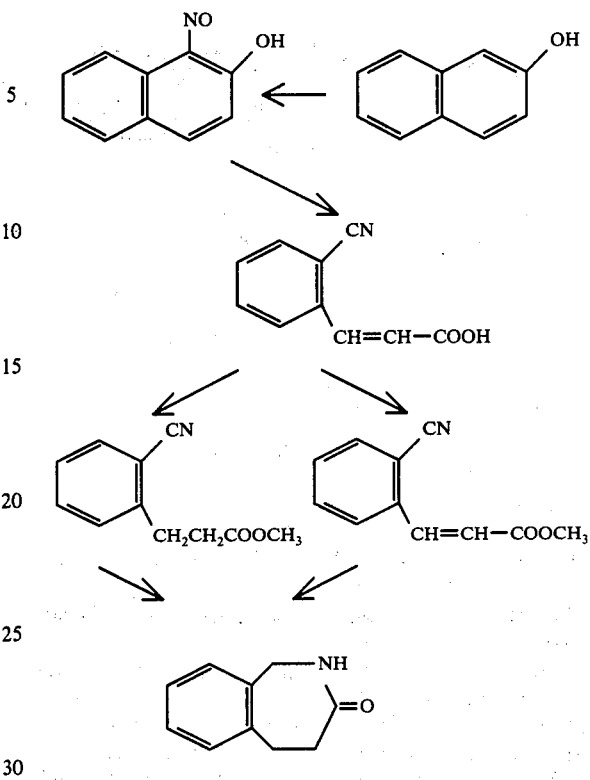

After recrystallization from carbon tetrachloride, the 1,2,4,5-tetrahydro-3H-2-benzazepin-3-one thus obtained had a melting point of 135°-136° C.

The work of these Russian authors did not report any substituted derivative of the fundamental bicyclic system.

In 1958, H. A. Bruson et. al. (J. Am. Chem. Soc. 80, (1958), 3633-36) mention the probability of obtaining the 1,1,5,5-tetramethyl derivative, whilst in 1970, P. C. Mukharji et al. (Indian J. Chem. 8, (1970), 225-9 and 318-24), on the sole basis of carbon and hydrogen analyses, stated that they isolated the following derivatives:

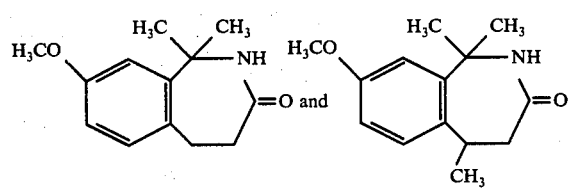

starting from the corresponding 3,4-dihydro-2(1H)-naphthalenones.

Structural proofs of the substituted products did not finally appear until the publication of the article by R. T. Conley et al. (J. Org. Chem. 28, (1963), 210-4) concerning the 1,1-dimethyl and 1,1,5,5-tetramethyl derivatives, which were also prepared from the corresponding 3,4-dihydro-2(1H)-naphthalenones and the more recent publication by R. R. Wittekind et. al. (J. Het. Chem. 8, (1971), 495-501) relating to five derivatives having methoxy radicals in both the 7- and 8-positions, which were prepared by the treatment of 3-(3,4-dimethoxyphenyl)-propionamide with benzaldehyde, s-trioxane and paraldehyde:

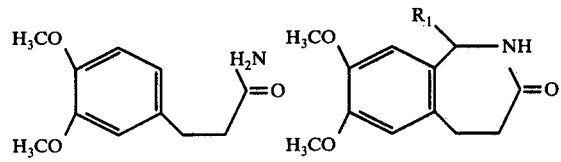
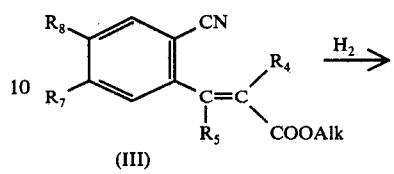

It is this last work that also describes the only N-substituted derivative hitherto isolated:

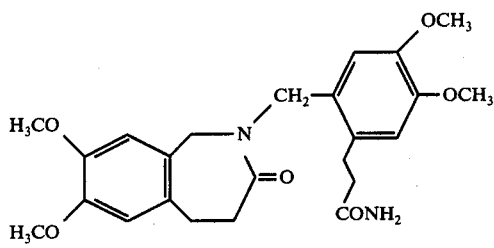

It was obtained in a yield of only 3% and was, in any case, produced unintentionally.

The absence of derivatives substituted in the 2- and 4-positions is also to be noted.

Furthermore, the pharmacological properties of the 1,2,4,5-tetrahydro-3H-2-benzazepin-3-ones synthetized in this way have not been examined by their authors, who generally prepared them as intermediates in the synthesis of the corresponding 2,3,4,5-tetrahydro-1H-2-benzazepines (see A. N. Kost et al., loc.cit., R. R. Wittekind et al., loc.cit.).

For the preparation of the compounds to which the present invention relates, it should be noted that the method used by the Russian authors starting from beta-naphtol does not enable a substituent to be introduced in the 1-position and, furthermore, is of very little interest, in view of the difficult availability of the starting materials. On the other hand, Wittekind's method appears to be limited to phenylpropionamides with electrondonor radicals on the benzene ring.

The 1,2,4,5-tetrahydro-3H-2-benzazepin-3-ones according to the present invention may be prepared by one of the following processes:

(a) By the catalytic hydrogenation of an alkyl 2-$R_4$-3-$R_5$-3-(4-$R_8$-5-$R_7$-2-cyanophenyl)propionate of formula (II), according to the following equation:

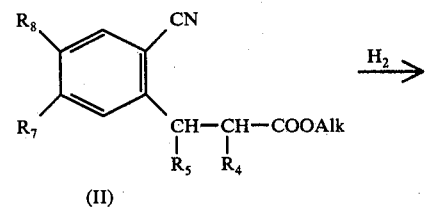

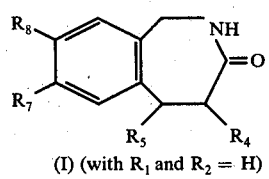

(I) (with $R_1$ and $R_2$ = H)

wherein $R_4$, $R_5$, $R_7$ and $R_8$ have the same meanings as above, at least one of these symbols being other than a hydrogen atom, and Alk represents a $C_1$-$C_4$-alkyl radical.

(b) By the catalytic hydrogenation of an alkyl 2-$R_4$-3-$R_5$-3-(4-$R_8$-5-$R_7$-2-cyanophenyl)-propenoate of formula (III), according to the following equation:

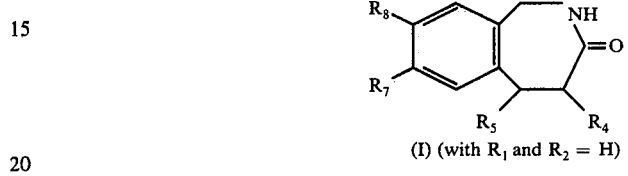

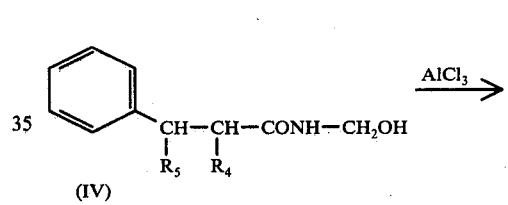

(I) (with $R_1$ and $R_2$ = H)

wherein $R_4$, $R_5$, $R_7$ and $R_8$ have the same meanings as above, at least one of these symbols being other than a hydrogen atom and Alk being a $C_1$-$C_4$-alkyl radical.

(c) By reacting a 2-$R_4$-3-$R_5$-N-hydroxymethyl-3-phenyl-propionamide of formula (IV) with aluminium trichloride, according to the following equation:

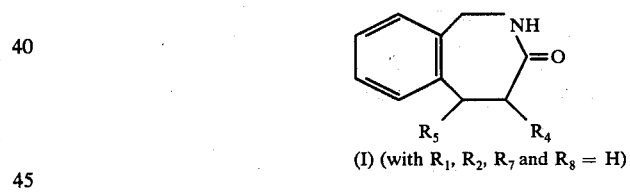

(I) (with $R_1$, $R_2$, $R_7$ and $R_8$ = H)

wherein $R_4$ and $R_5$ have the same meanings as above, at least one of these symbols being other than a hydrogen atom.

(d) By reacting benzaldehyde, in the presence of polyphosphoric acid (PPA), with a 2-$R_4$-3-$R_5$-3-(3-$R_7$-phenyl)-propionamide of formula (V), according to the following equation:

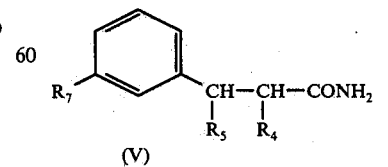

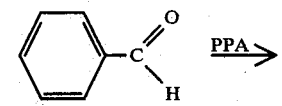

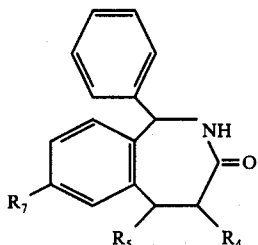

(I) (with $R_2$ and $R_8$ = H; $R_1$ = phenyl and $R_7$ = $C_1$-$C_5$-alkoxy)

wherein $R_4$ and $R_5$ have the same meanings as above, whereas $R_7$ is a $C_1$-$C_5$-alkoxy radical.

(e) By reacting an alkali metal derivative of a 1,2,4,5-tetrahydro-3H-2-benzazepin-3-one of formula (VI) with an $R_2$ halide of formula (VII), according to the following equation:

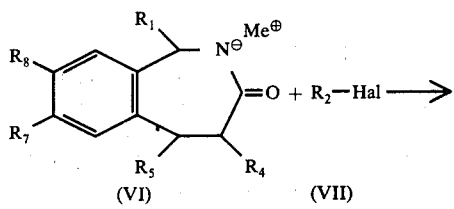

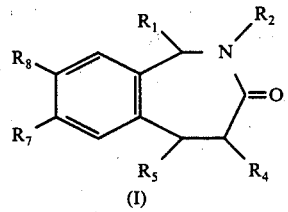

(I)

wherein $R_1$, $R_4$, $R_5$, $R_7$ and $R_8$ having the same meanings as above, $R_2$ is a straight or branched-chain alkyl radical, an alkenyl radical having 3 to 6 carbon atoms, an acyl radical having 1 to 4 carbon atoms, an alkoxyalkyl radical, a mono- or dialkylaminoalkyl radical, a cyanoalkyl radical, an alkoxyacetyl radical, an alkoxycarbonylalkyl radical or a (tetrahydro-2H-pyran-2-yloxy)alkyl radical, all the alkyl and the alkoxy radicals having 1 to 5 carbon atoms, whereas Hal represents a halogen atom such as chlorine or bromine and Me is an alkali metal atom.

(f) By reacting a 2-alkoxycarbonylalkyl-1,2,4,5-tetrahydro-3H-2-benzazepin-3-one of formula (VIII) with ammonia, according to the following equation:

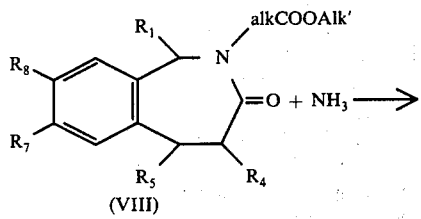

(VIII)

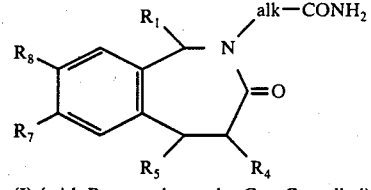

(I) (with $R_2$ = carbamoyl—$C_1$—$C_5$—alkyl)

wherein $R_1$, $R_4$, $R_5$, $R_7$ and $R_8$ have the same meanings as above, alk represents an alkylene radical having 1 to 5 carbon atoms and Alk' an alkyl radical having 1 to 5 carbon atoms.

(g) By hydrolysis in an aqueous acid medium of a 2[(tetrahydro-2H-pyran-2-yloxy)alkyl]-1,2,4,5-tetrahydro-3H-2-benzazepin-3-one of formula (IX), according to the following equation:

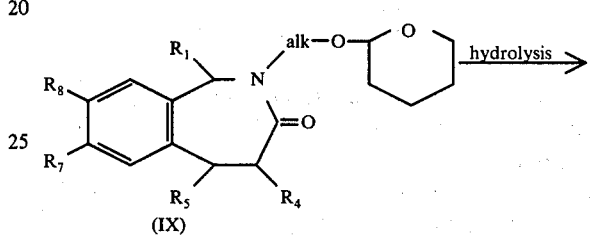

(IX)

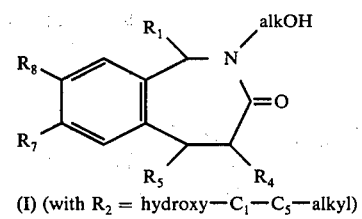

(I) (with $R_2$ = hydroxy—$C_1$—$C_5$—alkyl)

wherein $R_1$, $R_4$, $R_5$, $R_7$ and $R_8$ have the same meanings as given above and alk is an alkylene radical having 1 to 5 carbon atoms.

(h) By reacting a 1,2,4,5-tetrahydro-3H-2-benzazepin-3-one of formula (X) with an excess of acrylonitrile in the presence of a base, according to the following equation:

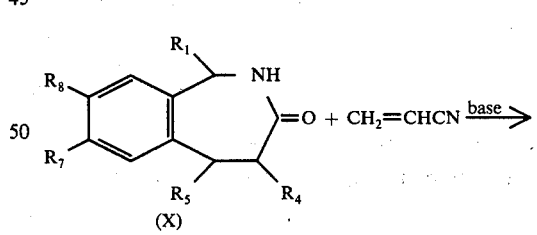

(X)

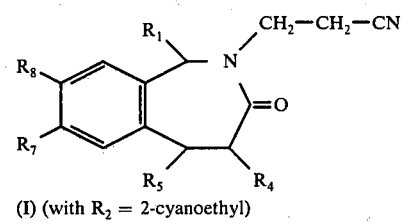

(I) (with $R_2$ = 2-cyanoethyl)

wherein $R_1$, $R_4$, $R_5$, $R_7$ and $R_8$ have the same meanings as above.

(i) By the hydrogenation of a 2-cyanoalkyl-1,2,4,5-tetrahydro-3H-2-benzazepin-3-one of formula (XI), in the presence of Raney nickel and anhydrous sodium acetate in acetic anhydride, according to the following equation:

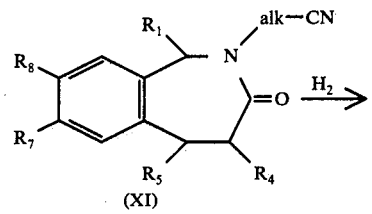
(XI)

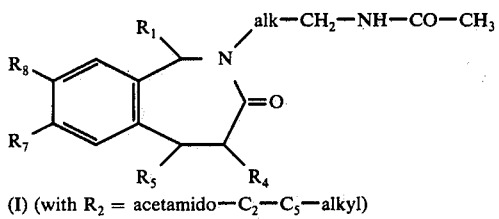
(I) (with $R_2$ = acetamido—$C_2$—$C_5$—alkyl)

wherein $R_1$, $R_4$, $R_5$, $R_7$ and $R_8$ have the same meanings as above and alk represents an alkylene radical having 1 to 4 carbon atoms.

(j) By hydrolysis in an acid medium of a 2-cyanoalkyl-1,2,4,5-tetrahydro-3H-2-benzazepin-3-one of formula (XI), according to the following equation:

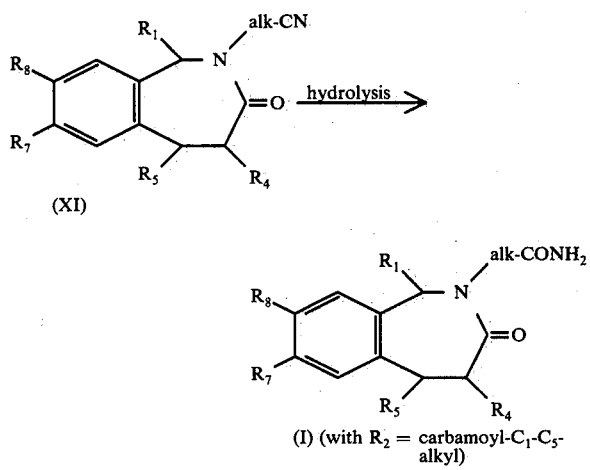
(XI)

(I) (with $R_2$ = carbamoyl-$C_1$-$C_5$-alkyl)

wherein $R_1$, $R_4$, $R_5$, $R_7$ and $R_8$ have the same meanings as above and alk represents an alkylene radical having 1 to 5 carbon atoms.

(k) By reacting a 1,2,4,5-tetrahydro-3H-2-benzazepin-3-one of formula (X) with an excess of formaldehyde, in the presence of a base, according to the following equation:

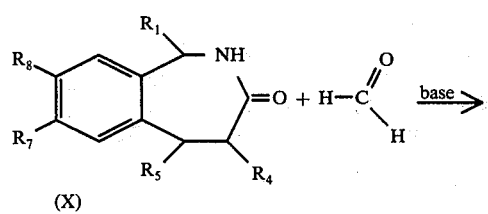
(X)

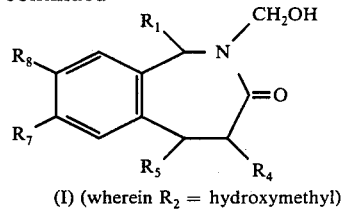
(I) (wherein $R_2$ = hydroxymethyl)

wherein $R_1$, $R_4$, $R_5$, $R_7$ and $R_8$ have the same meanings as above.

The compounds according to the present invention have valuable pharmaceutical properties and, in particular, have a beneficial activity on the mnemic processes and a protective activity against hypoxic type agressions. Therefore, their first use is in geropsychiatry, a field which is characterized by disorders of memory due not only to senile cellular alterations but also to a decrease in the supply of oxygen to the brain as a result of isolated or repeated vascular accidents (V. C. Hachinski, Lancet, II, (1974), 207).Furthermore, the compounds according to the present invention are useful in many other clinical indications, such as for the prevention and treatment of cerebro-vascular or cardio-vascular injuries, post-traumatic or toxic comas, memory disorders, difficulties of mental concentration and the like.

Action on the mnemic processes is shown particularly by the reduction in the time for spinal fixation, a test which has been described in the literature (see C. Giurgea and F. Mouravieff-Lesuisse, Arch. Int. Pharmacodyn, 191/2, (1971), 279) as an elementary model of memory which is endowed with a pharmacological reactivity in good correlation with clinical physiopathology. In the rat, after unilateral lesion of the cerebellum, there is a postural asymmetry of the hind paws. This asymmetry may persist, even after spinal section, if the animal has been in this situation for a sufficiently long time. This time, which is called the spinal fixation time, is 45 minutes under the experimental conditions. On the other hand, if spinal section is performed before the expiry of this period, for example 35 minutes after the onset of the asymmetry, the latter disappears. Animals treated with placebos do not retain this asymmetry under these conditions. Conversely, any product which allows the rats to retain the asymmetry (thus achieving spinal fixation) when the spinal section is carried out after 35 minutes, is regarded as being active.

Under these conditions, administration of a compound according to the present invention, for example 2-methyl-1,2,4,5-tetrahydro-3H-2-benzazepin-3-one (compound A), 2-carbamoylmethyl-1,2,4,5-tetrahydro-3H-2-benzazepin-3-one (compound B) and 5-phenyl-1,2,4,5-tetrahydro-3H-2-benzazepin-3-one (compound C) produces the following effects:

Compounds A, B and C, administered intraperitoneally at a dose of 17.5, 22 and 23.7 mg./kg., respectively, (0.1 mmole/kg. in all three cases) produce spinal fixation after 35 minutes in three animals out of five, two animals out of four and four animals out of five, respectively.

Under the same conditions, piracetam is active at a dose of 30 mg./kg. (0.2 millimole/kg.), at which dose it causes spinal fixation in four animals out of nine (see C. Giurgea and F. Mouravieff-Lesuisse, loc.cit.).

The action on the mnemic processes is also demonstrated by the ability of the compounds to improve another type of memory retention in the rat. The principle of the active avoidance test, which has been developed in our laboratories and used for this purpose, may be described as follows: the withdrawal reaction of a rat's paw subjected to an increasing and measured pressure is observed. The pressure at which the withdrawal reaction is produced is called the reaction threshold. The latter is expressed in grams and thus corresponds to the minimum pressure which, when applied to the paw of the animals, causes withdrawal. It is read off directly from a scale of the apparatus used. When tested 24 hours later, the control animals show no apparent retention of the previous test: the avoidance is produced at an intensity of stimulation comparable to that of the previous day. Conversely, animals treated with a compound which has a positive effect on the mnemic processes (for example piracetam) show a significant degree of retention: the stimulus to which the rats react by a reflex of avoidance is statistically lower than that of the control animals. Use is made of a minimum of 20 rats per test (10 treated rats and 10 control rats), the active dose being defined as the minimum dose which lowers the stimulus to below 110 g.

Subcutaneous administration of compounds according to the present invention, namely, 2-methyl-1,2,4,5-tetrahydro-3H-2-benzazepin-3-one (compound A), 7-methoxy-2-methyl-1,2,4,5-tetrahydro-3H-2-benzazepin-3-one (compound D), 4-methyl-2-pentyl-1,2,4,5-tetrahydro-3H-2-benzazepin-3-one (compound E) and 8-methyl-1,2,4,5-tetrahydro-3H-2-benzazepin-3-one (compound F), produces under these conditions the effects set out in the following Table I. This Table I shows that the compounds according to the present invention exert, in this test, an activity which is superior to that of piracetam.

TABLE I

| Compound | Subcutan.dose mg/kg. | Stimulus* | Active dose mg/kg. | Active dose mmole/kg. |
|---|---|---|---|---|
| A | 0 | 164 | | |
|   | 0.09 | 146 | | |
|   | 0.175 | 106 | 0.175 | 0.001 |
| D | 0 | 165 | | |
|   | 0.205 | 118 | | |
|   | 1 | 90 | 1 | 0.005 |
| E | 0 | 166 | | |
|   | 0.24 | 122 | | |
|   | 0.49 | 89 | 0.49 | 0.002 |
| F | 0 | 154 | | |
|   | 0.175 | 121 | | |
|   | 0.35 | 111 | | |
|   | 0.87 | 101 | 0.87 | 0.005 |
| piracetam | 0 | 153 | | |
|   | 1.5 | 120 | | |
|   | 3.5 | 90 | 3.5 | 0.025 |

*Stimulus (expressed in g.) initiating the avoidance reaction 24 hours after the first stimulation.

Protection against hypoxic type agressions, on the other hand, is demonstrated by a decrease in the lethality induced by a curarizing agent with a short duration of action, i.e. oxydipentonium chloride (Brevatonal). At the doses used, this curarizing agent brings about a respiratory depression which, in turn, brings about a hypoxi-hypercapnic syndrome. A compound capable of protecting the brain during this short period of hypoxia ensures survival. The compounds are administered to groups of 10 mice one hour before the injection of the curarizing agent; concurrently herewith, a control group of 10 mice is given a physiological salt solution prior to the curarizing agent. For each compound, the proportion of surviving mice is compared with the proportion of surviving control mice by the "Fisher exact probability test". This test, called the Brevatonal test, has also been developed in our laboratories.

Intraperitoneal administration (i.p.) of compounds according to the present invention, namely, 2-methyl-1,2,4,5-tetrahydro-3H-2-benzazepin-3-one (compound A), 2,4-dimethyl-1,2,4,5-tetrahydro-3H-2-benzazepin-3-one (compound G), 2-isobutyl-4-methyl-1,2,4,5-tetrahydro-3H-2-benzazepin-3-one (compound H), 7-chloro-2-methyl-1,2,4,5-tetrahydro-3H-2-benzazepin-3-one (compound J) 8-chloro-2-methyl-1,2,4,5-tetrahydro-3H-2-benzazepin-3-one (compound K) and 8-methyl-2-pentyl-1,2,4,5-tetrahydro-3H-2-benzazepin-3-one (compound L), produces under these conditions the effects set out in the following Table II. It can be seen from this Table II that the compounds according to the present invention have, at equal doses, an activity superior to that of piracetam:

TABLE II

| Compound | Dose mg/kg. (mmole/kg.) (i.p.) | Proportion of survivors treated animals | Proportion of survivors control animals | Fisher exact probability |
|---|---|---|---|---|
| A | 55 (0.32) | 7/10 | 0/10 | $P < 0.005$ |
| G | 2 (0.01) | 6/10 | 1/10 | $P < 0.05$ |
| H | 2 (0.01) | 9/10 | 2/10 | $P < 0.005$ |
|   | 7 (0.032) | 7/10 | 2/10 | $P < 0.05$ |
|   | 23 (0.1) | 9/10 | 1/10 | $P < 0.001$ |
| J | 21 (0.1) | 7/10 | 1/10 | $P < 0.01$ |
|   | 66 (0.32) | 8/10 | 1/10 | $P < 0.005$ |
| K | 21 (0.12) | 6/10 | 1/10 | $P < 0.05$ |
|   | 66 (0.37) | 6/10 | 1/10 | $P < 0.05$ |
| L | 78 (0.32) | 6/10 | 0/5 | $P < 0.05$ |
| piracetam | 45 (0.32) | 1/10 | 0/10 | not significant |
|   | 142 (1) | 4/10 | 2/10 | not significant |
|   | 454 (3.2) | 8/10 | 1/10 | $P < 0.005$ |

The $LD_{50}$ doses were determined intraperitoneally in the rat and calculated by using the method of Spearman-Karber (D. J. Finney, Statistical Methods in Biological Assay, pub. Griffin & Co., London, 1952, p. 524). By way of example, the $LD_{50}$ of compound A mentioned above is 760 mg./kg.

The compounds according to the present invention may be administered orally, parenterally or rectally, in admixture with solid or liquid pharmaceutical excipients or carriers.

Thus, in the case of oral administration, the forms used may be solid or liquid and may be presented as gelatine capsules, coated or uncoated tablets, pills, solutions or suspensions, in admixture with conventional pharmaceutical excipients or carriers. The excipients for tablets include, inter alia, lactose, potato starch, corn starch, talc, gelatine, cellulose and cellulose derivatives, sugar, silica, stearic acid, magnesium stearate, calcium stearate, polyethylene glycols and polyvinylpyrrolidone, as well as various coloring materials and flavorings.

For parenteral administration, the excipient or carrier must be a parenterally acceptable sterile liquid, for example water or a solution of polyvinylpyrrolidone, or an oil, for example peanut oil.

For rectal administration, the excipient or carrier is usually a suppository base component, for example, cocoa butter or a mixture of semi-glycerides.

The forms of administration are advantageously in the form of appropriate dosage units. Tablets, pills, gelatine capsules, vials and suppositories preferably contain a unit dose of from 50 to 500 mg. and solutions and suspensions preferably contain from 1 to 20% by weight of an active compound according to the invention.

The following Examples are given for the purpose of illustrating the present invention.

The chemical structure of all the compounds according to the present invention mentioned in the Examples has, in each case, been confirmed by infra-red, nuclear magnetic resonance and mass spectrometry.

EXAMPLE 1. (PROCESS (A))

washed with a little diethyl ether; a white solid separates out which is filtered off and recrystallized from methanol. Yield: 26% of theory of 8-chloro-4-methyl-1,2,4,5-tetrahydro-3H-2-benzazepin-3-one. M.P. 184°–185° C.

Analysis $C_{11}H_{12}ClNO$ (M.W. 209.6) Calculated: C, 63.1%; H, 5.77%; N, 6.68%. Found: C, 63.1%; H, 5.76%; N, 6.65%.

The following compounds are prepared in an analogous manner:

TABLE III

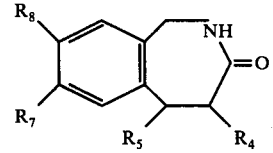

| $R_4$ | $R_5$ | $R_7$ | $R_8$ | M.P. (recryst. solvent) | Yield % | Analyses calculated % | found % |
|---|---|---|---|---|---|---|---|
| *H | H | H | H | 132–133° C. (methanol or CCl$_4$) | 65 | $C_{10}H_{11}NO$<br>C 74.5<br>H 6.88<br>N 8.69 | (M.W. 161.2)<br>74.7<br>6.92<br>8.57 |
| CH$_3$ | H | H | H | 136–137° C. (CCl$_4$) | 40 | $C_{11}H_{13}NO$<br>C 75.4<br>H 7.42<br>N 7.99 | (M.W. 175.2)<br>75.4<br>7.50<br>8.09 |
| C$_2$H$_5$ | H | H | H | 117–119° C. (CCl$_4$) | 40 | $C_{12}H_{15}NO$<br>C 76.2<br>H 7.94<br>N 7.40 | (M.W. 189.2)<br>76.1<br>7.90<br>7.35 |
| n-C$_4$H$_9$ | H | H | H | 85–87° C. (diisopropyl ether) | 31 | $C_{14}H_{11}NO$<br>C 77.4<br>H 8.75<br>N 6.45 | (M.W. 217.3)<br>77.6<br>9.0<br>6.45 |
| H | H | OCH$_3$ | H | 169–170° C. (CCl$_4$) | 35 | $C_{11}H_{13}NO_2$<br>C 69.1<br>H 6.80<br>N 7.32 | (M.W. 191.2)<br>69.2<br>6.86<br>7.28 |
| CH$_3$ | H | OCH$_3$ | H | 154–156° C (CCl$_4$) | 26 | $C_{12}H_{15}NO_2$<br>C 70.3<br>H 7.31<br>N 6.83 | (M.W. 205.2)<br>70.3<br>7.34<br>6.82 |
| H | H | H | Cl | 178–179° C. (methanol) | 33 | $C_{10}H_{10}ClND$<br>C 61.4<br>H 5.11<br>N 7.16 | (M.W. 195.6)<br>61.3<br>5.15<br>7.11 |
| H | H | Cl | H | 139–140° C. (ethanol) | 23 | $C_{10}H_{10}ClNO$<br>C 61.4<br>H 5.11<br>N 7.16 | (M.W. 195.6)<br>61.2<br>5.21<br>7.10 |
| CH$_3$ | H | Cl | H | 144–145° C. (2-propanol) | 12 | $C_{11}H_{12}ClNO$<br>C 63.1<br>H 5.77<br>N 6.68 | (M.W.209.6)<br>62.8<br>5.67<br>7.0 |
| C$_2$H$_5$ | H | Cl | H | 141–142° C. (CCl$_4$) | 19 | $C_{12}H_{14}ClNO$<br>C 64.4<br>H 6.30<br>N 6.26 | (M.W.223.7)<br>64.4<br>6.27<br>6.22 |
| H | CH$_3$ | H | H | 128–130° C. (2-propanol) | 68 | $C_{11}H_{13}NO$<br>C 75.5<br>H 7.48<br>N 7.99 | (M.W.175.2)<br>75.7<br>7.50<br>7.94 |
| CH$_3$ (cis) | CH$_3$ | H | H | 126–128° C. | 60 | $C_{12}H_{15}NO$<br>C 76.2<br>H 7.99<br>N 7.40 | (M.W.189.2)<br>76.1<br>8.05<br>7.36 |

*This compound, which is known per se (see A.N. Kost and A.P. Stankevicius, loc.cit.), is not claimed. Furthermore, it does not have the pharmacological properties of the compounds according to the present invention. However, it may be used as a starting material for the preparation of the compounds according to the present invention which are substituted on the nitrogen atom in the 2-position (processes (e) to (k) mentioned above).

8-Chloro-4-methyl-1,2,4,5-tetrahydro-3H-2-benzazepin-3-one

A solution of 39.2 g. (0.16 moles) of methyl 3-(4-chloro-2-cyanophenyl)-2-methylpropionate in 1 liter of anhydrous methanol is introduced into a 2 liter autoclave. About 5 g. of W-5 Raney nickel are added and the mixture is stirred for 24 hours under a hydrogen pressure (initial pressure 3.5 bars). The reaction mixture is filtered, the catalyst is washed with chloroform and the solvent is removed in vacuo. The residue obtained is Methyl 3-(4-chloro-2-cyanophenyl)-2-methylpropionate used as starting material in Example 1 is new. It can be obtained by heating, while stirring, for 45 minutes at 220° C. a mixture of 132 g. (0.45 moles) of methyl 3-(2-bromo-4-chlorophenyl)-2-methylpropionate, 61.5 g. (0.68 moles) of cuprous cyanide, 51 ml. of pyridine and 1 ml. of benzonitrile. The reaction mixture is then taken up several times with toluene, filtered over active carbon and the filtrate evaporated to dryness. The oily residue finally obtained is purified by distillation. B.P.

116°-120° C./0.6 mm.Hg. There are obtained 78.4 g. (73% of theory) of methyl 3-(4-chloro-2-cyanophenyl)-2-methylpropionate.

Analysis $C_{12}H_{12}ClNO_2$ (M.W. 237.7) Calculated: C, 60.7%; H, 5.05%. Found: C, 60.7%; H, 5.03%.

Purity by gel permeation chromatography (GPC): 97%.

The following new compounds are prepared in an analogous manner:

Table IV

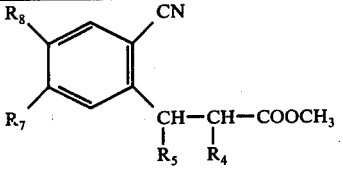

| $R_4$ | $R_5$ | $R_7$ | $R_8$ | B.P.° C./mmHg; GPC purity | Yield % |
|---|---|---|---|---|---|
| H | H | H | H | 104/0.2; 93% | 58 |
| $CH_3$ | H | H | H | 85–94/0.01; 97% | 45 |
| $C_2H_5$ | H | H | H | 88–96/0.01; 97% | 55 |
| n-$C_4H_9$ | H | H | H | 116–119/0.15; 98% | 74 |
| H | H | $OCH_3$ | H | 140/0.15; 99% | 32 |
| $CH_3$ | H | $OCH_3$ | H | 120–126/0.05; 95% | 44 |
| H | H | H | Cl | 112–118/0.2; 93% | 44 |
| H | H | Cl | H | 99–104/0.08; 90% | 32 |
| $CH_3$ | H | Cl | H | 107–109.0.25; 83% | 49 |
| $C_2H_5$ | H | Cl | H | 120/0.6; 94% | 72 |
| H | $CH_3$ | H | H | 100–102/0.08; 97% | 81 |
| $CH_3$ | $CH_3$ | H | H | 96/0.1; 98% | 82 |

Methyl 3-(2-bromo-4-chlorophenyl)-2-methylpropionate, used as starting material in the preceding stage, is also new. It is obtained by reacting 3-(2-bromo-4-chlorophenyl)-2-methylpropionic acid with thionyl chloride in benzene solution, while stirring, at reflux temperature, the acid chloride thus formed then being reacted with methanol in benzene solution. After removing the solvents in vacuo, the residual oil is purified by distillation. B.P. 116–118° C./0.1 mm.Hg. Yield: 60% of theory of methyl 3-(2-bromo-4-chlorophenyl)-2-methylpropionate.

Analysis $C_{11}H_{12}BrClO_2$ (M.W. 291.5) Calculated: C, 45.3%; H, 4.14%. Found: C, 45.5%; H, 4.0%.

GPC purity: 98%.

The following compounds are prepared in an analogous manner:

TABLE V

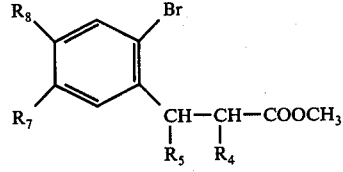

| $R_4$ | $R_5$ | $R_7$ | $R_8$ | B.P.° C./mmHg; GPC purity | Yield % |
|---|---|---|---|---|---|
| H | H | H | H | 87/0.02; 99% 148–149/12 | 93 |
| $CH_3$ | H | H | H | 148/12; 99% | 95 |
| $C_2H_5$ | H | H | H | 146/12; 99% | 95 |
| n-$C_4H_9$ | H | H | H | 168–170/12; 99% | 88 |
| H | H | $OCH_3$ | H | 114/0.15; 99% | 90 |
| $CH_3$ | H | $OCH_3$ | H | 116–118/0.01; 99% | 77 |
| H | H | H | Cl | 140/0.8; 99% | 84 |
| H | H | Cl | H | 90–92/0.15; 98% | 86 |
| $CH_3$ | H | Cl | H | 106–108/0.6; 99% | 60 |
| $C_2H_5$ | H | Cl | H | 100–103/0.01; 99% | 80 |
| H | $CH_3$ | H | H | 108–109/1.5; 99% | 90 |
| $CH_3$ | $CH_3$ | H | H | 109–110/0.15; 98% | 86 |

3-(2-Bromo-4-chlorophenyl)-2-methylpropionic acid used as a starting product in the preceding stage is also new. It is obtained by saponifying diethyl (2-bromo-4-chlorobenzyl)methyl-malonate with potassium hydroxide in aqueous alcoholic solution at reflux temperature, followed by decarboxylation of the diacid formed by heating at 165° C. The overall yield is 79% of theory of 3-(2-bromo-4-chlorophenyl)-2-methylpropionic acid, which is in the form of an oil.

Analysis $C_{10}H_{10}BrClO_2$ (M.W. 277.5) Calculated: C, 43.3%; H, 3.60%. Found: C, 42.9%; H, 3.40%.

The following compounds are prepared in an analogous manner:

TABLE VI

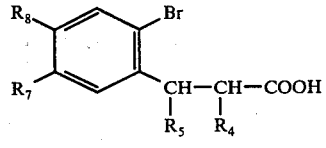

| $R_4$ | $R_5$ | $R_7$ | $R_8$ | M.P.(recryst. solvent) | Yield % |
|---|---|---|---|---|---|
| H | H | H | H | 91–93° C. (cyclohexane) | 95 |
| $CH_3$ | H | H | H | liquid | 80 |
| $C_2H_5$ | H | H | H | liquid | 38 |
| n-$C_4H_9$ | H | H | H | liquid | 42 |
| H | H | $OCH_3$ | H | 81–83° C | 95 |
| $CH_3$ | H | $OCH_3$ | H | liquid | 95 |
| H | H | H | Cl | liquid | 85 |
| H | H | Cl | H | liquid | 80 |
| $CH_3$ | H | Cl | H | liquid | 78 |
| $C_2H_5$ | H | Cl | H | liquid | 66 |
| H | $CH_3$ | H | H | liquid | 86 |
| $CH_3$ | $CH_3$ | H | H | liquid | 94 |

The penultimate compound of the above Table VI has been described in literature ($R_4$, $R_7$, $R_8$ = H, $R_5$ = $CH_3$) (see J. Klein et al., J. Org. Chem. 22, (1957), 1019-21).

The diethyl (2-bromo-4-chlorobenzyl)methyl-malonate used as a starting material in the preceding stage is also new. It is prepared by adding slowly 2-bromo-4-chlorobenzyl bromide, while stirring, to an ethanolic solution of the sodium salt of diethyl methyl-malonate. The reaction is carried out while cooling in an ice-bath and is completed by heating for 3 hours under reflux. A liquid is obtained which is purified by distillation in vacuo, B.P. 135°–145° C./0.15 mmHg. Yield: 57% of theory of diethyl (2-bromo-4-chlorobenzyl)methyl-malonate.

Analysis $C_{15}H_{18}BrClO_4$ (M.W. 377.6) Calculated: C, 47.7%; H, 4.77%. Found: C, 48.0%; H, 4.50%.

GPC purity: 99%.

The following compounds are prepared in an analogous manner:

TABLE VII

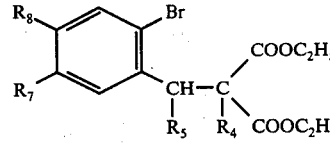

| $R_4$ | $R_5$ | $R_7$ | $R_8$ | B.P.° C./mmHg; GPC purity | Yield % |
|---|---|---|---|---|---|
| H | H | H | H | 123–134/0.01; 95% | 65 |
| $CH_3$ | H | H | H | 114–124/0.05; 93% | 65 |
| $C_2H_5$ | H | H | H | 136–138/0.01; 99% | 67 |
| n-$C_4H_9$ | H | H | H | 138–140/0.25; 99% | 75 |
| H | H | $OCH_3$ | H | 147–150/0.25; 99% | 64 |
| $CH_3$ | H | $OCH_3$ | H | 135–140/0.01; 90% | 61 |
| H | H | H | Cl | 147–150/0.8; 99% | 45 |
| H | H | Cl | H | 152–170/0.25; 90% | 45 |
| $CH_3$ | H | Cl | H | 145–150/0.25; 98% | 66 |

TABLE VII-continued

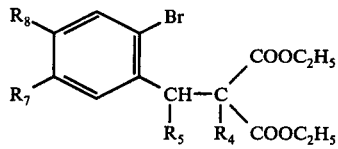

| R$_4$ | R$_5$ | R$_7$ | R$_8$ | B.P.° C./mmHg; GPC purity | Yield % |
|---|---|---|---|---|---|
| C$_2$H$_5$ | H | Cl | H | 137/0.01; 99% | 80 |
| H | CH$_3$ | H | H | 128/0.1; 99% | 90 |
| CH$_3$ | CH$_3$ | H | H | 127/0.1; 99% | 54 |

The penultimate compound in the above Table VII has been described in literature (R$_4$, R$_7$, R$_8$ = H, R$_5$ = CH$_3$) (see J. Klein et al., J. Org. Chem., 22, (1957), 1019-27).

2-Bromo-4-chlorobenzyl bromide used in the preceding stage has been described in German Offenlegungsschrift No. 1,944,335. It is obtained by the dropwise addition, under ultra-violet irradiation, of a slight excess of bromine to 2-bromo-4-chlorotoluene at 160° C. 2-Bromo-4-chlorobenzyl bromide, in the form of a liquid, is isolated by distillation in vacuo. B.P. 142°–144° C./12 mmHg. Yield: 55% of theory.

The two following compounds are prepared in an analogous manner. The first one has been described in literature (see J. V. Supniewski et. al., J. Am. Chem. Soc. 48, (1926), 516), whilst the second one is new:

2-bromobenzyl bromide. B.P. 121°–123° C/12mmHg. Yield 63% of theory 2-bromo-5-chlorobenzyl bromide. B.P. 154° C/12 mmHg. M.P. 67°–68° C.
(after recrystallization from hexane). Yield 41% of theory.

When the benzene ring contains a methoxy radical, bromination is carried out under reflux in carbon tetrachloride, using N-bromosuccinimide in the presence of benzoyl peroxide. Starting, for example, from 2-bromo-5-methoxytoluene, a solid product is obtained which can be purified by recrystallization from cyclohexane. M.P. 87°–89° C. The yield is 59% of theory of 2-bromo-5-methoxybenzyl bromide. This compound has been described in literature (see R. Breslow et. al., J. Am. Chem. Soc. 90, (1968), 4051-55).

Analysis C$_8$H$_8$Br$_2$O (M.W. 280.0) Calculated: C, 34.3%; H, 2.85%; Br, 57.1%. Found: C, 34.4%; H, 2.90%; Br, 57.2%.

1-Bromo-2-(1-bromoethyl)-benzene used in lieu of the above 2-bromobenzyl bromides when a methyl radical is to be introduced as R$_5$ (see the two last compounds of Table VII), is also a new compound. It is prepared by the reaction of phosphorus tribromide, in the presence of pyridine, with o-bromo-alpha-methyl-benzyl alcohol. The reaction is carried out in dry benzene, whilst cooling in an ice bath, by the slow addition of the alcohol to the reaction medium which is vigorously stirred. After the separation of the organic phase, drying and distillation in vacuo, 1-bromo-2-(1-bromoethyl)-benzene is obtained as a liquid in a yield of 75% of theory. B.P. 124° C./12 mm.Hg.

EXAMPLE 2 (PROCESS (B)).

8-Methyl-1,2,4,5-tetrahydro-3H-2-benzazepin-3-one

A solution of 27 g. (0.13 moles) of methyl trans-2-cyano-4-methylcinnamate in 1 liter dry methanol is introduced into a 2-liter autoclave. About 5 g. of W-5 Raney nickel are added and the mixture is stirred for 17 hours under a hydrogen pressure (initial pressure 3.5 bars). The reaction mixture is filtered, the catalyst is washed with chloroform and the solvent is removed in vacuo. The red residue obtained is washed with about 20 ml. of 2-propanol and then taken up in hot 2-propanol, whereafter the solution is decolorized over active carbon. After recrystallization, 12.4 g. (53% of theory) of 8-methyl-1,2,4,5-tetrahydro-3H-2-benzazepin-3-one are obtained. M.P. 174°–175° C.

Analysis C$_{11}$H$_{13}$NO (M.W. 175.1) Calculated: C, 75.4%; H, 7.43%; N, 7.99%. Found: C, 75.4%; H, 7.51%; N, 8.02%.

Methyl trans-2-cyano-4-methyl-cinnamate used as starting material in Example 2 is a new compound. It can be obtained by heating, with stirring, for 1 hour at 220° C., a mixture of 60 g. (0.23 moles) of methyl trans-2-bromo-4-methyl-cinnamate, 31.7 g. (0.35 moles) of cuprous cyanide, 27 ml. of pyridine and 0.5 ml. of benzonitrile. The reaction mixture is taken up in toluene, filtered over active carbon and then evaporated to dryness. The same series of operations is carried out with diethyl ether. After recrystallization from methanol of the residual solid, 27.3 g. (58% of theory) of crystalline, solid methyl trans-2-cyano-4-methyl-cinnamate are obtained. M.P. 95°–96° C.

Analysis C$_{12}$H$_{11}$NO$_2$ (M.W. 201.2) Calculated: C, 71.6%; H, 5.51%; N, 6.95%. Found: C, 70.9%; H, 5.42%; N, 7.09%.

Methyl trans-2-bromo-4-methyl-cinnamate used as starting material in the preceding stage is also a new compound. It is prepared by reacting, with stirring, trans-2-bromo-4-methyl-cinnamic acid with thionyl chloride in benzene solution at reflux temperature to give the corresponding acid chloride which is then reacted with methanol in benzene solution. The reaction mixture is evaporated to dryness to give solid methyl trans-2-bromo-4-methyl-cinnamate in a yield of 99% of theory. M.P. 70° C.

Analysis C$_{11}$H$_{11}$BrO$_2$ (M.W. 255.1) Calculated: C, 51.8%; H, 4.31%. Found: C, 51.8%; H, 4.28%.

2-Bromo-4-methyl-cinnamic acid used in the preceding stage has been described by S. Munavalli and G. Ourisson (Bull. Soc. Chim. France, 1964, 3103-12) and can be prepared by the process described by them. The $^1$H NMR spectrum of the compound shows that it has the trans configuration (DMSO-d$_6$) —CH$_A$=CH$_B$—COOCH$_3$ system; $\delta_A$ = 7.90, $\delta_B$ = 6.56, J$_{AB}$ = 16 H$_z$; $\delta$ = 2.33 (3, S, aryl CH$_3$).

EXAMPLE 3 (PROCESS (C))

5-Phenyl-1,2,4,5-tetrahydro-3H-2-benzazepin-3-one 8.7 g. (0.065 moles) of aluminium chloride are added to a solution of 7.7 g. (0.030 moles) of N-hydroxymethyl-3,3-diphenyl-propionamide in 300 ml. of nitrobenzene. The reaction mixture is heated, with stirring, at 100° C. for 6 hours and then cooled and poured into 1 liter water containing 5 ml. of concentrated hydrochloric acid. The nitrobenzene is removed by steam distillation and the residue is extracted with chloroform. The organic phase is dried over anhydrous sodium sulfate and then evaporated to dryness. The residual solid is purified by chromatography on a silica column, using a mixture of benzene and ethanol (85:15 v/v) as eluent, and then recrystallized from 2-propanol. 2.4 g. (34% of theory) of 5-phenyl-1,2,4,5-tetrahydro-3H-2-benzazepin-3-one are obtained. M.P. 182°–183° C.

Analysis $C_{16}H_{15}NO$ (M.W. 237.3) Calculated: C, 81.0%; H, 6.37%; N, 5.90%. Found: C, 81.0%; H, 6.37%; N, 5.86%.

N-hydroxymethyl-3,3-diphenyl-propionamide used as starting material in Example 3 is a new compound. It is obtained by reacting excess paraformaldehyde and 3,3-diphenylpropionamide, in the presence of sodium ethoxide, in carbon tetrachloride at reflux temperature. Reflux heating is maintained for 2 to 3 hours and then the reaction mixture is evaporated to dryness. The solid N-hydroxymethyl-3,3-diphenyl-propionamide obtained is recrystallized from ethyl acetate. M.P. 149°–151° C. The yield is 64% of theory.

Analysis $C_{16}H_{17}NO_2$ (M.W. 255.3) Calculated: C, 75.3%; H, 6.71%; N, 5.49%. Found: C, 75.1%; H, 6.54%; N, 5.53%.

3,3-Diphenylpropionamide is a known compound; its preparation and physical properties are descibed in literature.

EXAMPLE 4 (PROCESS (D))

7-Methoxy-1-phenyl-1,2,4,5-tetrahydro-3H-2-benzazepin-3-one

To a mixture of 73 g. of phosphorus pentoxide and 43.5 ml. of 85% phosphoric acid, rendered homogeneous by heating at 170° C., is added at room temperature a solution of 9.0 g. (0.05 moles) of 3-(3-methoxyphenyl)-propionamide and 5.9 g. (0.055 moles) of benzaldehyde in 104 ml. of glacial acetic acid. Stirring under an atmosphere of nitrogen is maintained for 3 days and then the reaction mixture is poured into 1 liter water; a precipitate appears, which is filtered off, washed neutral with water and dried. After separation by chromatography and recrystallization from ethanol, 1.5 g. (11% of theory) of pure 7-methoxy-1-phenyl-1,2,4,5-tetrahydro-3H-2-benzazepin-3-one is obtained. M.P. 185–186° C.

Analysis $C_{17}H_{17}NO_2$ (M.W. 267.3) Calculated: C, 76.4%; H, 6.41%; N, 5.24%. Found: C, 76.4%; H, 6.38%; N, 5.26%.

The amide used in this preparation, which was already been described in the literature, can be synthetized from the known, corresponding carboxylic acid in known manner.

EXAMPLE 5 (PROCESS (E))

2,8-Dimethyl-1,2,4,5-tetrahydro-3H-2-benzazepin-3-one 0.023 moles of sodium hydride is added slowly, while stirring, to a solution of 2.0 g. (0.011 moles) of 8-methyl-1,2,4,5-tetrahydro-3H-2-benzazepin-3-one in 60 ml. of dimethylformamide, followed by heating at 80° C. for 80 minutes. The reaction mixture is cooled in an ice bath and 6.5 g. (0.046 moles) of methyl iodide added dropwise, the rate of addition being regulated so as to maintain the temperature of the reaction mixture at about 10° C. When the addition is complete, the temperature is raised slowly to 60° C. and then maintained at this level for 3 hours. The reaction mixture is evaporated to dryness in vacuo and the solid residue is extracted with chloroform. The organic solution is washed twice with water, dried over anhydrous sodium sulfate, filtered and then evaporated to dried over anhydrous sodium sulfate, filtered and then evaporated to dryness in vacuo. The solid residue is taken up in diisopropyl ether, filtered over active carbon and recrystallized from diisopropyl ether. 2,8-Dimethyl-1,2,4,5-tetrahydro-3H-2-benzazepin-3-one is obtained in a yield of 55% of theory. M.P. 75°–76° C.

Analysis $C_{12}H_{15}NO$ (M.W. 189.2) Calculated: C, 76.2%; H, 7.99%; N, 7.40%. Found: C, 76.1%; H, 8.00%; N, 7.32%.

If methyl iodide is replaced by pentyl bromide, 8-methyl-2-pentyl-1,2,4,5-tetrahydro-3H-2-benzazepin-3-one is obtained in the same way in a yield of 67% of theory. M.P. 95°–97° C. (after recrystallization from diisopropyl ether).

Analysis $C_{16}H_{23}NO$ (M.W. 245.4) Calculated: C, 78.3%; H, 9.44%; N, 5.70%. Found: C, 78.2%; H, 9.43%; N, 5.69%.

The compounds set out in the following Tables VIII, IX, X and XI are prepared in an analogous manner; the $R_2$-halide used is given in each case:

TABLE VIII

| $R_4$ | $R_5$ | $R_2$ | Reagent | M.P. (recryst. solvent) | Yield % | Analyses calculated % | found % |
|---|---|---|---|---|---|---|---|
| H | H | $C_2H_5$ | $C_2H_5I$ | 85–87° C. (benzene + hexane) | 26 | $C_{12}H_{15}NO$<br>C 76.2<br>H 7.99<br>N 7.40 | (M.W.189.2)<br>76.5<br>8.20<br>7.20 |
| $C_2H_5$ | H | $CH_3$ | $CH_3I$ | 95–96° C. (diisopropyl ether) | 50 | $C_{13}H_{17}NO$<br>C 76.8<br>H 8.37<br>N 6.89 | (M.W.203.2)<br>76.9<br>8.40<br>6.86 |
| $CH_3$ | H | $CH_3$ | $CH_3I$ | 97–99° C. (diisopropyl ether) | 84 | $C_{12}H_{15}NO$<br>C 76.2<br>H 7.99<br>N 7.40 | (M.W.189.2)<br>76.1<br>7.98<br>7.36 |
| $CH_3$ | H | $C_5H_{11}$ | $C_5H_{11}Br$ | 63–64° C. (hexane) | 71 | $C_{16}H_{23}NO$<br>C 78.3<br>H 9.38<br>N 5.71 | (M.W.245.3)<br>78.2<br>9.40<br>5.80 |
| H | H | $CH_3$ | $CH_3I$ | 89–90° C. (diisopropyl ether) | 33 | $C_{11}H_{13}NO$<br>C 75.4<br>H 7.48<br>N 7.99 | (M.W.175.2)<br>75.6<br>7.42<br>7.99 |

TABLE VIII-continued

| $R_4$ | $R_5$ | $R_2$ | Reagent | M.P. (recryst. solvent) | Yield % | calculated % | found % |
|---|---|---|---|---|---|---|---|
| $CH_3$ | H | $CH_2CH(CH_3)-CH_3$ | iso-$C_4H_9Br$ | 65–66° C. (diisopropyl ether) | 35 | $C_{15}H_{21}NO$<br>C 77.9<br>H 9.15<br>N 6.06 | (M.W.231.3)<br>77.9<br>9.12<br>6.09 |
| H | $C_6H_5$ | $CH_3$ | $CH_3I$ | 188–189° C. (methanol) | 40 | $C_{17}H_{17}NO$<br>C 81.2<br>H 6.82<br>N 5.57 | (M.W.251.3)<br>80.7<br>6.47<br>5.48 |
| n-$C_4H_9$ | H | $CH_3$ | $CH_3I$ | 63.5–64.5° C. (hexane) | 91 | $C_{15}H_{21}NO$<br>C 77.9<br>H 9.15<br>N 6.05 | (M.W.231.3)<br>78.3<br>9.79<br>6.49 |
| n-$C_4H_9$ | $C_5H_{11}$ | $C_5H_{11}Br$ | | liquid | 69 | $C_{19}H_{29}NO$<br>C 79.4<br>H 10.2<br>N 4.87 | (M.W.287.5)<br>79.1<br>10.4<br>4.67 |
| H | $CH_3$ | $CH_3$ | $CH_3I$ | 84–85° C. (diisopropyl ether) | 80 | $C_{12}H_{15}NO$<br>C 76.2<br>H 7.99<br>N 7.40 | (M.W.189.2)<br>76.1<br>8.04<br>7.38 |
| H | $CH_3$ | $C_5H_{11}$ | $C_5H_{11}Br$ | liquid | 75 | $C_{16}H_{23}NO$<br>C 78.3<br>H 9.38<br>N 5.71 | (M.W.245.3)<br>78.2<br>9.60<br>5.66 |
| H | $CH_3$ | $CH_2-CH=CH_2$ | allyl Br | 50–51° C. (diisopropyl ether) | 28 | $C_{14}H_{17}NO$<br>C 78.1<br>H 7.96<br>N 6.50 | (M.W.215.3)<br>78.2<br>7.92<br>6.48 |
| $CH_3$ (cis) | $CH_3$ | $CH_3$ | $CH_3I$ | 103–104° C. (diisopropyl ether) | 50 | $C_{13}H_{17}NO$<br>C 76.8<br>H 8.37<br>N 6.89 | (M.W.203.2)<br>76.7<br>8.50<br>6.85 |
| $CH_3$ (cis) | $CH_3$ | $C_5H_{11}$ | $C_5H_{11}Br$ | liquid | 39 | $C_{17}H_{25}NO$<br>C 78.7<br>H 9.64<br>N 5.40 | (M.W.259.4)<br>78.7<br>9.70<br>5.37 |
| H | $CH_3$ | $CH_2OCH_3$ | $CH_3OCH_2Cl$ | liquid | 68 | $C_{13}H_{17}NO_2$<br>C 71.2<br>H 7.76<br>N 6.39 | (M.W.219.2)<br>71.1<br>7.80<br>6.41 |
| $CH_3$ | H | $(CH_2)_2OCH_3$ | $CH_3O(CH_2)_2Cl$ | liquid | 50 | $C_{14}H_{19}NO_2$<br>C 72.1<br>H 8.21<br>N 6.00 | (M.W.233.3)<br>72.0<br>8.18<br>6.10 |
| H | H | $CH_2CN$ | $NCCH_2Cl$ | 98–99° C. (2-propanol) | 18 | $C_{12}H_{12}N_2O$<br>C 72.0<br>H 6.04<br>N 14.0 | (M.W.200.2)<br>72.0<br>6.04<br>14.0 |
| $CH_3$ | H | $(CH_2)_3N(CH_3)_2$ | $(CH_3)_2N(CH_2)_3Cl$ | liquid | 25 | $C_{16}H_{24}N_2O$<br>C 73.9<br>H 9.30<br>N 10.8 | (M.W.260.4)<br>73.9<br>9.29<br>10.8 |

TABLE IX

| $R_1$ | $R_4$ | $R_2$ | Reagent | M.P. (recryst. solvent) | Yield % | calculated % | found % |
|---|---|---|---|---|---|---|---|
| $C_6H_5$ | H | | $CH_3I$ | 170–171° C. (methanol) | 49 | $C_{18}H_{19}NO_2$<br>C 76.8<br>H 6.81 | (M.W.281.3)<br>76.9<br>6.90 |

TABLE IX-continued

Structure: benzazepinone with $CH_3O$ at position shown, $R_1$, $R_2$ (on N), =O, $R_4$

| $R_1$ | $R_4$ | $R_2$ | Reagent | M.P. (recryst. solvent) | Yield % | Analyses calculated % | found % |
|---|---|---|---|---|---|---|---|
| H | $CH_3$ | $CH_3$ | $CH_3I$ | 140–142° C. (methanol) | 64 | N 4.98  $C_{13}H_{17}NO_2$  C 71.2  H 7.76 | 4.92 (M.W.219.2) 71.2 7.80 |
| H | H | $CH_3$ | $CH_3I$ | 116–118° C. (2-propanol) | 49 | N 6.39  $C_{12}H_{15}NO_2$  C 70.2  H 7.32  N 6.82 | 6.35 (M.W.205.2) 70.0 7.40 6.79 |

TABLE X

Structure: benzazepinone with Cl substituent, $R_2$ on N, =O, $R_4$

| $R_1$ | $R_4$ | $R_2$ | Reagent | M.P. (recryst.) | Yield | Analyses calculated | found |
|---|---|---|---|---|---|---|---|
| H | $CH_3$ | | $CH_3I$ | 81–83° C. (diisopropyl ether) | 52 | $C_{11}H_{12}ClNO$  C 63.1  H 5.77  N 6.68 | (M.W.209.6) 62.9 5.90 6.70 |
| H | $C_5H_{11}$ | | $C_5H_{11}Br$ | 95–97° C. (diisopropyl ether) | 57 | $C_{15}H_{20}ClNO$  C 67.8  H 7.59  N 5.27 | (M.W.265.7) 67.6 7.63 5.20 |
| $CH_3$ | $CH_3$ | | $CH_3Ii$ | 139–140° C. (diisopropyl ether) | 67 | $C_{12}H_{14}ClNO$  C 64.4  H 6.30  N 6.26 | (M.W.223.7) 64.4 6.34 6.23 |
| $CH_3$ | $C_5H_{11}$ | | $C_5H_{11}Br$ | 105–106° C. (diisopropyl ether) | 50 | $C_{16}H_{22}ClNO$  C 68.7  H 7.92  N 5.00 | (M.W.279.8) 68.7 8.01 4.95 |

TABLE XI

Structure: benzazepinone with Cl substituent, $R_2$ on N, =O, $R_4$

| $R_4$ | $R_2$ | Reagent | M.P. (recryst. solvent) | c,128 Yield % | Analyses calculated % | found % |
|---|---|---|---|---|---|---|
| H | $CH_3$ | $CH_3I$ | 101–103° C. (diisopropyl ether) | 62 | $C_{11}H_{12}ClNO$  C 63.1  H 5.77  N 6.68 | M.W.209.5 62.9 5.91 6.70 |
| $CH_3$ | $C_5H_{11}$ | $C_5H_{11}Br$ | 75.5–76.5° C. (diisopropyl ether) | 56 | $C_{16}H_{22}ClNO$  C 68.7  H 7.92  N 5.00 | (M.W.279.8) 68.7 8.00 4.94 |
| $C_2H_5$ | $CH_3$ | $CH_3I$ | 84–86° C. (diisopropyl ether) | 20 | $C_{13}H_{16}ClNO$  C 65.7  H 6.78  N 5.89 | (M.W.237.5) 65.6 6.80 5.82 |

EXAMPLE 6 (PROCESS (E))

8-Chloro-2-(ethoxyacetyl)-4-methyl-1,2,4,5-tetrahydro-3H-2-benzazepin-3-one 0.018 moles of sodium hydride is added slowly, with stirring, to a solution of 3.4 g. (0.016 moles) of 8-chloro-4-methyl-1,2,4,5-tetrahydro-3H-2-benzazepin-3-one in 60 ml. of dimethylformamide. The reaction mixture is heated to 80° C. for 15 minutes and then cooled in an ice bath. While cooling, 2.2 g. (0.018 moles) of ethoxyacetyl chloride are added dropwise and then the reaction mixture is gradually brought to a temperature of 80° C. and maintained at this temperature for 3 hours. The reaction mixture is then cooled, evaporated to dryness in vacuo and the residue extracted with chloroform. The organic solution is washed twice with water, dried over anhydrous sodium sulfate, filtered and then evaporated to dryness in vacuo. The residual solid is purified by chromatography on a silica column, using a mixture of benzene/ethanol (9:1 v/v) as eluent, and it is then recrystallized from 2-propanol. 2.5 g. (52% of theory) of 8-chloro-2-(ethoxyacetyl)-4-methyl-1,2,4,5-tetrahydro-3H-2-benzazepin-3-one are obtained. M.P. 123°–124° C.

Analysis $C_{15}H_{18}ClNO_3$ (M.W. 295.5) Calculated: C, 61.0%; H, 6.14%; N, 4.74%. Found: C, 61.0%; H, 6.10%; N, 4.71%.

The compounds set out in the following Table XII are prepared in an analogous manner:

TABLE XII

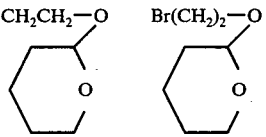

| $R_4$ | $R_8$ | $R_2$ | Reagent | M.P. (recryst solvent) | Yield % | Analyses calculated % | found % |
|---|---|---|---|---|---|---|---|
| H | H | $COCH_3$ | $CH_3COBr$ | 144–146° C. (diisopropyl ether) | 10 | $C_{12}H_{13}NO_2$ C 70.9 H 6.39 N 6.89 | (M.W.203.2) 70.9 6.42 6.25 |
| H | H | $CH_2COOC_2H_5$ | $CH_2Cl$<br>\|<br>$COOC_2H_5$ | liquid | 65 | $C_{14}H_{17}NO$ C 68.0 H 6.87 N 5.66 | (M.W.247.3) 68.2 6.74 5.59 |
| $CH_3$ | Cl | 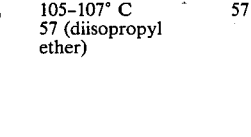 $CH_2CH_2$—O | $Br(CH_2)_2$—O (same pyranyl group) | 105–107° C 57 (diisopropyl ether) | 57 | $C_{18}H_{24}ClNO_3$ C 64.0 H 7.16 N 4.14 | (M.W.337.8) 65.1 7.20 4.10 |

EXAMPLE 7 (PROCESS (F))

2-Carbamoylmethyl-1,2,4,5-tetrahydro-3H-2-benzazepin-3-one

Ammonia gas is bubbled, while cooling in an ice bath, into a solution of 2.3 g. (0.0093 moles) of 2-carbethoxymethyl-1,2,4,5-tetrahydro-3H-2-benzazepin-3-one in 250 ml. of methanol. When saturation is reached, the reaction mixture is brought to room temperature and left to stand for 2 days. It is then filtered and the solvent is removed in vacuo. The solid residue is recrystallized from ethanol to give 2-carbamoylmethyl-1,2,4,5-tetrahydro-3H-2-benzazepin-3-one in a yield of 64% of theory. M.P. 156°–158° C.

Analysis $C_{12}H_{14}N_2O_2$ (M.W. 218.2) Calculated: C, 66.0%; H, 6.47%; N, 12.8%. Found: C, 66.0%; H, 6.60%; N, 13.0%.

EXAMPLE 8 (PROCESS (G))

8-Chloro-2-(2-hydroxyethyl)-4-methyl-1,2,4,5-tetrahydro-3H-2-benzazepin-3-one 150 ml. of 20% sulfuric acid are added, with vigorous stirring, to a solution of 2.9 g. (0.0086 moles) of 8-chloro-4-methyl-2-[2-(tetrahydro-2H-pyran-2-yloxy)ethyl]-1,2,4,5-tetrahydro-3H-2-benzazepin-3-one in 50 ml. of dichloromethane. When the addition is complete, stirring is continued for 2 at room temperature. After decantation, the organic phase is washed neutral with water, dried over anhydrous sodium sulfate and then evaporated to dryness in vacuo. The solid residue is purified by chromatography on a silica column and then by recrystallization from methanol. 8-Chloro-2-(2-hydroxyethyl)-4-methyl-1,2,4,5-tetrahydro-3H-2-benzazepin-3-one is obtained in a yield of 10% of theory. M.P. 139°–140° C.

Analysis $C_{13}H_{16}ClNO_2$ (M.W. 253.7) Calculated: C, 61.5%; H, 6.35%; N, 5.51%. Found: C, 61.5%; H, 6.40%; N, 5.47%.

EXAMPLE 9 (PROCESS (H))

2-(2-Cyanoethyl)-5-methyl-1,2,4,5-tetrahydro-3H-2-benzazepin-3-one

To a mixture of 6 g. (0.034 moles) of 5-methyl-1,2,4,5-tetrahydro-3H-2-benzazepin-3-one and 4 drops of Triton B (benzyltrimethylammonium hydroxide) in 10 ml. of pyridine, are added dropwise 2 g. (0.038 moles) of acrylonitrile dissolved in 2.5 ml. of pyridine. The reaction mixture is heated to 80° C. for 2 hours and then poured into iced water. It is acidified with hydrochloric acid to pH 4 and extracted with chloroform. The organic phase is washed neutral with water and then dried over anhydrous sodium sulfate. It is filtered and the solvent is evaporated off in vacuo. 8 g. (almost theoretical yield) of syrupy 2-(2-cyanoethyl)-5-methyl-1,2,4,5-tetrahydro-3H-2-benzazepin-3-one are obtained.

Analysis $C_{14}H_{16}N_2O$ (M.W. 228.3) Calculated: C, 73.6%; H, 7.02%; N, 12.3%. Found: C, 73.6%; H, 7.10%; N, 12.2%.

The compounds set out in the following Table XIII are prepared in an analogous manner:

TABLE XIII

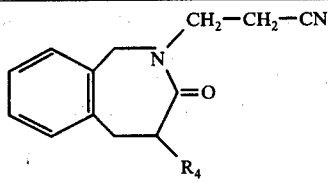

| R₄ | M.P. (recryst.solv.) | Yield % | Analyses calculated % | found % |
|---|---|---|---|---|
| CH₃ | 80–81° C. (diisopropyl ether) | 51 | $C_{14}H_{16}N_2O$<br>C 73.6<br>H 7.02<br>N–12.3 | (M.W. 228.3)<br>73.6<br>6.99<br>12.0 |
| n-C₄H₉ | 66–67° C. (diisopropyl) | 77 | $C_{17}H_{22}N_2O$<br>C 75.5<br>H 8.20<br>N 10.4 | (M.W. 270.3)<br>76.2<br>8.27<br>11.2 |

EXAMPLE 10 (PROCESS (I))

2-(3-Acetamidopropyl)-5-methyl-1,2,4,5-tetrahydro-3H-2-benzazepin-3-one

A solution of 8 g. (0.034 moles) of 2-(2-cyanoethyl)-5-methyl-1,2,4,5-tetrahydro-3H-2-benzazepin-3-one in 220 ml. of acetic anhydride is introduced into a 2-liter autoclave, 12 g. of anhydrous sodium acetate and approximately 5 g. of W-5 -Raney nickel, washed twice with 20 ml. of acetic anhydride, are added thereto. The reaction mixture is brought to a temperature of 50° C. and then stirred for 4 hours under a hydrogen pressure (initial pressure of 3.5 bars). The reaction mixture is filtered, the catalyst is washed with a little acetic anhydride, and the solvent is evaporated in vacuo. The residual oil is suspended in water and the pH of the mixture is adjusted to 8 by the addition of aqueous sodium hydroxide solution. It is extracted with chloroform and the organic phase is washed with water and dried over anhydrous sodium sulfate. The syrup obtained after filtration and evaporation of the solvent in vacuo is purified by chromatography on a silica column. 7 g. (74% of theory) of syrupy 2-(3-acetamidopropyl)-5-methyl-1,2,4,5-tetrahydro-3H-2-benzazepin-3-one are obtained.

Analysis $C_{16}H_{22}N_2O_2$ (M.W. 274.4) Calculated: C, 70.0%; H, 8.08%; N, 10.2%. Found: C, 70.1%; H, 8.10%; N, 10.1%.

EXAMPLE 11 (PROCESS (J))

2-(2-Carbamoylethyl)-4-methyl-1,2,4,5-tetrahydro-3H-2-benzazepin-3-one

A solution of 2.1 g. (0.0092 moles) of 2-(2-cyanoethyl)-4-methyl-1,2,4,5-tetrahydro-3H-2-benzazepin-3-one in 5 ml. of 35% hydrochloric acid is heated for 30 minutes at 40° C., while stirring. The reaction mixture is poured into 30 ml. of water and the pH adjusted to 9 by the addition of sodium carbonate, with vigorous stirring. The precipitate formed is washed with water, dried and then recrystallized from diisopropyl ether. 1.5 g. (66% of theory) of 2-(2-carbamoylethyl)-4-methyl-1,2,4,5-tetrahydro-3H-2-benzazepin-3-one is obtained. M.P. 168°–169° C.

Analysis $C_{14}H_{18}N_2O_2$ (M.W. 246.3) Calculated: C, 68.3%; H, 7.36%; N, 11.4%. Found: C, 68.0%; H, 7.54%; N, 10.8%.

EXAMPLE 12 (PROCESS (K))

cis-4,5-Dimethyl-2-hydroxymethyl-1,2,4,5-tetrahydro-3H-2-benzazepin-3-one

A solution of 5.7 g. (0.030 moles) of cis-4,5-dimethyl-1,2,4,5-tetrahydro-3H-2-benzazepin-3-one, 9 ml. (0.09 moles) of 35% aqueous formaldehyde solution and 0.05 g. of sodium hydroxide in 50 ml. of 92% ethanol is heated for 5 hours at 80° C., while stirring. The reaction mixture is cooled and the solvents are evaporated off in vacuo. The oil obtained is taken up in chloroform, washed several times with water and then dried over anhydrous sodium sulfate. After evaporation of the solvent in vacuo, the residual syrup is purified by recrystallization from diisopropyl ether. 4 g. (61% of theory) of cis-4,5-dimethyl-2-hydroxymethyl-1,2,4,5-tetrahydro-3H-2-benzazepin-3-one are obtained. M.P. 91°–92° C.

Analysis $C_{13}H_{17}NO_2$ (M.W. 219.3) Calculated: C, 71.2%; H, 7.81%; N, 6.39%. Found: C, 72.4%; H, 7.56%; N, 6.44%.

In the same way, 2-hydroxymethyl-1,2,4,5-tetrahydro-3H-2-benzazepin-3-one is obtained in a yield of 40% of theory. M.P. 109°–110° C. (after recrystallization from 2-propanol).

Analysis $C_{11}H_{13}NO_2$ (M.W. 191.2) Calculated: C, 69.1%; H, 6.85%; N, 7.32%. Found: C, 69.6%; H, 6.90%; N, 7.37%.

and 2-hydroxymethyl-4-methyl-1,2,4,5-tetrahydro-3H-2-benzazepin-3-one is obtained in a yield of 34% of theory. M.P. 114°–116° C. (after recrystallization from acetone).

Analysis $C_{12}H_{15}NO_2$ (M.W. 205.3) Calculated: C, 70.2%; H, 7.36%; N, 6.82%. Found: C, 70.5%; H, 7.34%; N, 6.80%.

We claim:

1. A 1,2,4,5-tetrahydro-3H-2-benzazepin-3-one having the formula

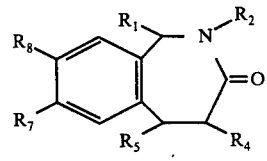

wherein
R₁ is a hydrogen atom or phenyl,
R₂ is a hydrogen atom, straight-chain or branched chain alkyl, alkenyl having 3 to 6 carbon atoms, alkanoyl having 1 to 4 carbon atoms, hydroxyalkyl, alkoxyalkyl, monoalkylaminoalkyl, dialkylaminoalkyl, cyanoalkyl, alkoxyacetyl, carbamoylalkyl, acetamidoalkyl, alkoxycarbonylalkyl or (tetrahydro-2H-pyran-2-yloxy) alkyl, the terms alkyl and alkoxy, however used, either alone or as part of the definition of a more complex substituent, have 1 to 5 carbon atoms, except in the case of acetamidoalkyl where alkyl has 2 to 5 carbon atoms, $R_5$ is a hydrogen atom, alkyl having 1 to 4 carbon atoms or phenyl, $R_7$ is a hydrogen or halogen atom or alkoxy having 1 to 4 carbon atoms, $R_8$ is a hydrogen or halogen atom or alkyl having 1 to 4 carbon atoms, at least one of the symbols $R_1$ to $R_8$ being other than a hydrogen atom.

2. A compound as claimed in claim 1, namely 2-methyl-1,2,4,5-tetrahydro-3H-2-benzazepin-3-one.

3. A compound as claimed in claim 1, namely 2-carbamoylmethyl-1,2,4,5-tetrahydro-3H-2-benzazepin-3-one.

4. A compound as claimed in claim 1, namely 5-phenyl-1,2,4,5-tetrahydro-3H-2-benzazepin-3one.

5. A compound as claimed in claim 1, namely 7-methoxy-2-methyl-1,2,4,5-tetrahydro-3H-2-benzazepin-3-one.

6. A compound as claimed in claim 1, namely 4-methyl-2-pentyl-1,2,4,5-tetrahydro-3H-2-benzazepin-3-one.

7. A compound as claimed in claim 1, namely 8-methyl-1,2,4,5-tetrahydro-3H-2-benzazepin-3-one.

8. A compound as claimed in claim 1, namely 2,4-dimethyl-1,2,4,5-tetrahydro-3H-2-benzazepin-3-one.

9. A compound as claimed in claim 1, namely 2-isobutyl-4-methyl-1,2,4,5-tetrahydro-3H-2-benzazepin-3-one.

10. A compound as claimed in claim 1, namely 7-chloro-2-methyl-1,2,4,5-tetrahydro-3H-2-benzazepin-3-one.

11. A compound as claimed in claim 1, namely 8-chloro-2-methyl-1,2,4,5-tetrahydro-3H-2-benzazepin-3-one.

12. A compound as claimed in claim 1, namely 8-methyl-2-pentyl-1,2,4,5-tetrahydro-3H-2-benzazepin-3-one.

13. A composition having a beneficial activity on the mnemic processes and a protective activity against hypotoxic type aggressions comprising an effective amount for said uses of a 1,2,4,5-tetrahydro-3H-2-benzazepin-3-one having the formula

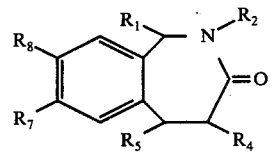

wherein $R_1$ is a hydrogen atom or phenyl, $R_2$ is a hydrogen atom, straight-chain or branched-chain alkyl, alkenyl having 3 to 6 carbon atoms, alkanoyl having 1 to 4 carbon atoms, hydroxy alkyl, alkoxyalkyl, monoalkylaminoalkyl, dialkylaminoalkyl, cyanoalkyl, alkoxyacetyl carbamoylalkyl, acetamidoalkyl, alkoxycarbonylalkyl or (tetrahydro-2H-pyran-2-yloxy) alkyl, the terms alkyl and alkoxy, however used, either alone or as part of the definition of a more complex substituent, have 1 to 5 carbon atoms, except in the case of acetamidoalkyl, where alkyl has 2 to 5 carbon atoms, $R_4$ is a hydrogen atom or alkyl having 1 to 4 carbon atoms, $R_5$ is a hydrogen atom, alkyl having 1 to 4 carbon atoms or phenyl, $R_7$ is a hydrogen or halogen atom or alkoxy having 1 to 4 carbon atoms, $R_8$ is a hydrogen or halogen atom or an alkyl radical having 1 to 4 carbon atoms, at least one of the symbols $R_1$ to $R_8$ being other than a hyrogen atom, in admixture with a pharmaceutically acceptable solid or liquid carrier.

* * * * *

UNITED STATES PATENT OFFICE
CERTIFICATE OF CORRECTION

Patent No. 4,080,449            Dated March 21, 1978

Inventor(s) Paul Croisier et al.

It is certified that error appears in the above-identified patent and that said Letters Patent are hereby corrected as shown below:

Claim 4, line 2, change "3one" to -- 3-one --.

Signed and Sealed this

Twenty-sixth Day of September 1978

[SEAL]

Attest:

RUTH C. MASON
Attesting Officer

DONALD W. BANNER
Commissioner of Patents and Trademarks

UNITED STATES PATENT OFFICE
CERTIFICATE OF CORRECTION

Patent No. 4,080,449  Dated March 21, 1978

Inventor(s) Paul Croisier and Ludovic Rodriguez

It is certified that error appears in the above-identified patent and that said Letters Patent are hereby corrected as shown below:

Claim 1, between lines 9 and 10, insert the following:

-- $R_4$ is a hydrogen atom or alkyl having 1 to 4 carbon atoms --.

Claim 13, line 3, change "hypotoxic" to -- hypoxic --;

line 5 under the formula, change "hydroxy al-" to -- hydroxyal- --;

line 7 under the formula, after "alkoxyacetyl" insert a comma (,).

Signed and Sealed this

Sixteenth Day of January 1979

[SEAL]

Attest:

RUTH C. MASON
*Attesting Officer*

DONALD W. BANNER
*Commissioner of Patents and Trademarks*